United States Patent
Weisenfluh et al.

(10) Patent No.: US 9,757,324 B2
(45) Date of Patent: Sep. 12, 2017

(54) EMU OIL IN COMBINATION WITH OTHER ACTIVE INGREDIENTS FOR TREATING SKIN IMPERFECTIONS

(71) Applicants: Scott A. Weisenfluh, Taylor, PA (US); Ketan Desai, Easton, PA (US); Sandra Kroposky, Moosic, PA (US)

(72) Inventors: Scott A. Weisenfluh, Taylor, PA (US); Ketan Desai, Easton, PA (US); Sandra Kroposky, Moosic, PA (US)

(*) Notice: Subject to any disclaimer, the term of this patent is extended or adjusted under 35 U.S.C. 154(b) by 0 days.

(21) Appl. No.: 14/807,959

(22) Filed: Jul. 24, 2015

(65) Prior Publication Data

US 2016/0184215 A1 Jun. 30, 2016

Related U.S. Application Data

(62) Division of application No. 13/156,308, filed on Jun. 8, 2011, now Pat. No. 9,138,446.

(51) Int. Cl.
| | |
|---|---|
| A61K 8/92 | (2006.01) |
| A61K 35/57 | (2015.01) |
| A61Q 7/00 | (2006.01) |
| A61Q 19/00 | (2006.01) |
| A61K 8/49 | (2006.01) |
| A61K 8/63 | (2006.01) |

(52) U.S. Cl.
CPC ............ *A61K 8/925* (2013.01); *A61K 8/4953* (2013.01); *A61K 8/63* (2013.01); *A61K 35/57* (2013.01); *A61Q 7/00* (2013.01); *A61Q 19/00* (2013.01)

(58) Field of Classification Search
CPC .......... A61K 35/57; A61K 8/63; A61K 8/925; A61K 8/4953; A61Q 7/00; A61Q 19/00
See application file for complete search history.

(56) References Cited

U.S. PATENT DOCUMENTS

| | | | |
|---|---|---|---|
| 7,371,407 B2 | 5/2008 | Farmer | |
| 7,790,768 B2* | 9/2010 | Gan | A61K 8/44 424/70.1 |
| 2007/0048386 A1 | 3/2007 | Mallozzi et al. | |
| 2009/0186095 A1* | 7/2009 | Bowers Bahney | A61K 35/12 424/522 |
| 2011/0144141 A1* | 6/2011 | Hu | A61K 8/361 514/275 |
| 2014/0322148 A1* | 10/2014 | Jackson | A61K 31/506 424/59 |

FOREIGN PATENT DOCUMENTS

| | | |
|---|---|---|
| WO | 2012103037 A1 | 8/2012 |
| WO | 2012129499 A1 | 9/2012 |

* cited by examiner

*Primary Examiner* — Robert Cabral
(74) *Attorney, Agent, or Firm* — Andrews Kurth Kenyon LLP; David Bradin

(57) ABSTRACT

Compositions comprising emu oil as a vehicle for the delivery of other active ingredients for the treatment of cosmetic and other skin imperfections such as acne, wrinkles, and hair loss are disclosed. Methods of treating cosmetic and other skin imperfections using the compositions are also disclosed.

6 Claims, No Drawings

EMU OIL IN COMBINATION WITH OTHER ACTIVE INGREDIENTS FOR TREATING SKIN IMPERFECTIONS

This application claims priority to U.S. Utility patent application Ser. No. 13/156,308, the contents of which are hereby incorporated by reference in its entirety for all purposes.

BACKGROUND OF THE INVENTION

Emu oil has been used for hundreds of years by the native aborigines of Australia as a salve, because of its unique properties that allow it to deeply penetrate the epidermis. Studies have corroborated that Emu oil is non-comedogenic, has anti-inflammatory properties, is deeply moisturizing, and deeply penetrating.

A variety of topical agents are used to treat various disorders, such as acne, wrinkles, and alopecia. It would be advantageous to have compositions which increase the ability of these agents to penetrate the skin, so as to improve their activity. The present invention provides such compositions, and methods for their use.

SUMMARY OF THE INVENTION

Compositions comprising various active and cosmetic ingredients in emu oil are disclosed, as well as methods of treating various disorders, including skin disorders, using the compositions. The compositions include emu oil and various active ingredients to treat a variety of skin diseases and imperfections. The compositions use the penetrating properties of emu oil to augment the efficacy of the active and cosmetic ingredients, resulting in an enhanced effect.

In various embodiments of the invention, the active ingredients include:

One or more of Doxycycline, Erythromycin, Salicylic Acid, Sulphacetamide Sodium, Retin-A, Retinols, Retinoids, Azelaic acid, Clindamycin, Tazarotene, and Benzoyl Peroxide for treating acne;

One or both of Finasteride and Minoxidil for treating hair loss/alopecia;

Steroid creams and lotions, such as hydrocortisone butyrate, for treating various skin diseases that are commonly treated with steroids, including, but not limited to, psoriasis, atopic dermatitis, and contact dermatitis;

Retinol for wrinkles, and one or more of Acetyl Hexapeptide-3, Acetyl Glutamyl Heptapeptide, Palmitoyl Pentapeptide-3, Palmitoyl Oligopeptide, Terapeptide-3 and Dimethylaminoethanol, which reportedly act through stimulation of collagen and elastin as well as possessing anti-oxidant activity, to provide firming and improve the overall health appearance of the skin, and to remove wrinkles;

Glycolic acid for treating sun damage.

Alpha hydroxy acids, beta hydroxy acids and Kojic acid for exfoliating the skin and stimulating the cell production in the dermis, which results in a "plumper" thicker dermal layer by stimulating collagen and elastin production. This results in a smooth appearance of the skin as well as elimination of fine lines and wrinkles. Through the exfoliation process they also work well to remove/decrease hyperpigmentation, which can be hormonally or solar induced.

Green Tea as a pore size reducer, a hydrating agent, and an anti-oxidant.

Copper peptide for treating xerosis of the skin, removing scars, and providing antioxidant properties.

Idebenone and Ubiquinone—which have antioxidant activity that helps remove free radical damage and allows for the resumption of healthy tissue regeneration.

Human growth hormone for replacement therapy, and increasing skin vigor and tone.

DETAILED DESCRIPTION

Emu oil is obtained from a large, approximately five feet tail, flightless bird of Australia known as an Emu, *Dromideius novaehollandiae*. Emus are farmed for their meat, which is low in cholesterol and fat. The oil rendered from the Emu is actually a semi-solid fat (i.e., fat and oil mixture) at room temperature, but will herein be referred to as an oil.

The fat and oil mixture is stripped from the carcass of the Emu and can be melted to further liquefy the oil. Emu oil obtained in this manner is yellow in color and is olfactorially offensive. It is possible, through refining processes well known to those of skill in the art, to remove the yellow color from the oil and reduce its odor. PCT/AU91/00517 refers to removing the yellow color from Emu oil by exposing it to sunlight, page 8, and by subjecting it to chemical oxidation by mixing it with benzoyl peroxide in an organic solvent, page 9.

Emu Oil can be obtained from any commercial source such as TheScienceLab (above), EmuMagic (Nevis, Minn.), Wonder Oil Products, Inc (Milddleton, Calif.), Uniquely Emu Products Inc (Ottawa, Ill.), etc. The active ingredients can be obtained from various suppliers, and mixed with Emu Oil by simple vortexing. In the description below, all concentrations are weight/weight of the additive to emu oil, unless otherwise indicated.

Treatment of Skin Disorders

The compositions described herein can be used to treat acne and other skin disorders, in particular, for use in the following therapeutic fields:

1) for treating dermatological conditions and afflictions linked to a disorder of keratinization involving differentiation and proliferation, in particular for treating acne vulgaris, comedonic or polymorphic acne, acne rosacea, nodulocystic acne, acne conglobata, senile acne, secondary acnes, such as solar, drug or occupational acne, or hidradenitis suppurativa, 2) for treating other types of disorders of keratinization, in particular ichthyoses, ichthyosiform conditions, Darier's disease, palmoplantar keratoderma, leukoplakia and leucoplakiform conditions, or cutaneous or mucosal (oral) lichen, 3) for treating other dermatological conditions linked to a disorder of keratinization with an inflammatory and/or immunoallergic component and, in particular, all forms of psoriasis, whether cutaneous, mucosal or ungual, and even psoriatic rheumatism, or alternatively cutaneous atopy, such as eczema, or respiratory atopy or alternatively gingival hypertrophy; the compounds can also be used in some inflammatory conditions not exhibiting disorder of keratinization, such as folliculitis, 4) for treating all dermal or epidermal proliferations, whether they are benign or malignant and whether they are or are not of viral origin, such as common warts, flat warts, molluscum contagiosum and epidermodysplasia verruciformis, florid or oral papillomatoses, and the proliferations which can be induced by ultraviolet radiation, in particular in the case of actinic keratoses, 5) for repairing or combating skin aging, whether photoinduced or chronologic, or for reducing pigmentations, or any pathology associated with chronologic or actinic aging;

6) for preventively or curatively treating disorders of cicatrization or skin ulcers, for preventing or repairing stretch marks, or alternatively for promoting cicatrization, 7) for combating disorders of the sebaceous function, such as hyperseborrhoea of acne or simple seborrhoea, 8) in the treatment of any condition of fungal origin on the skin, such as tinea pedis and tinea versicolor, 9) in the treatment of dermatological conditions with an immunological component, 10) in the treatment of skin disorders due to exposure to UV radiation.

The compositions according to the invention are particularly useful for the preventive or curative treatment of acne vulgaris.

Treatment of Acne

When used to treat acne, the compositions can include an antibiotic, salicyclic acid and/or salicylates, benzoyl peroxide, and the like.

The salicylic acid or salicylates can be in the form of a natural extract or as a pure compound. Examples of extracts that include salicylates include willow bark and aspen bark.

Salicylic acid is a keratolytic agent; promotes desquamation, clears blockages, helps prevent new lesions, & improves skin texture and hyperpigmentation after break-outs. The presence of salicylates also helps reduce the acidity of the salicylic acid, by providing a buffer. That is, when an acid (in this case, salicylic acid) and its conjugate base (in this case, salicylates) are present in a formulation, each buffers the other, according to the well-known Henderson-Hasselbach equation (pH=pKa+log (concentration of acid/concentration of base).

Any cosmetically-acceptable salt of salicylic acid (i.e., salicylate) can be used in the formulations described herein. Representative salts include, but are not limited to, salts with cations of ammonium, sodium, potassium, magnesium, calcium, strontium, barium, aluminum, iron, zinc, bismuth and organic amines. A salt with at least one of these cations is preferable. More preferable is a sodium, potassium, magnesium or zinc salt, still more preferable is a sodium, potassium or zinc salt, and particularly preferable is a sodium salt.

The salicylic acid can be obtained from various suppliers, such as Parchem, USA, and the combination used to treat acne. Salicylic acid, typically in dry powder form, can be mixed with Emu Oil in a concentration of about 2%. In use, the mixture is applied once or twice daily on the acne lesion till resolution. In one embodiment, the active ingredient is doxycycline hyclate or doxycycline monohydrate, which can be obtained from Mylan laboratories, and the combination is used to treat acne. The concentration of active ingredient in the Emu Oil ranges from about 1 mg to about 100 mg per 100 cc of Emu Oil. The mixtures are to be applied once or twice daily on the acne lesion till resolution. In this and other embodiments, resolution of the acne lesion will be readily and visibly apparent to the patient to whom the composition is applied.

In another embodiment, the active ingredient is erythromycin, which can be obtained from various suppliers such as Abbott Labs, USA (EES Granules), and the combination is used to treat acne. Erythromycin, typically in dry powder form, can be mixed with Emu Oil in a concentration of between about 1% and about 2% by weight. In use, the mixture is applied once or twice daily on the acne lesion until resolution.

Clindamycin can be obtained from suppliers such as Dermik, USA. The powder is mixed with Emu Oil in a concentration of 10 mg/100 ml. The mixture is to be applied once or twice daily on the acne lesion till resolution.

In yet another embodiment, the active ingredient is sulphacetamide sodium, which can be obtained from suppliers such Shreejee Pharma, India. The sulphacetamide sodium, typically in dry powder form, is mixed with Emu Oil in a concentration of about 10%. The mixtures are applied once or twice daily on the acne lesion till resolution.

In yet another embodiment, the active ingredient is tretinoin, which can be obtained from suppliers such as Lozada Enterprises, USA. The tretinoin is typically supplied in cream form, and the cream is mixed with Emu Oil in a concentration of about 0.025% to about 0.1%. The mixture is applied once or twice daily on the acne lesion till resolution.

In yet another embodiment, the active ingredient is azelaic acid, which can be obtained from suppliers such as Triveni Chemicals, India. The azelaic acid, typically in the form of a powder, is mixed with Emu Oil in a concentration of around 20%. The mixture is applied once or twice daily on the acne lesion till resolution.

Tazarotene can be obtained from suppliers such as Aurochem laboratories, India. The powder is mixed with Emu Oil in a concentration of 0.05-0.1%. The mixture is to be applied once or twice daily on the acne lesion till resolution.

Benzoyl Peroxide can be obtained from suppliers such as Alfa Aesar, USA. The powder is mixed with Emu Oil in a concentration of between about 2.5 to about 10%. The mixture is to be applied once or twice daily on the acne lesion till resolution.

Other representative anti-acne agents that can be used, in addition to the salicylic acid and salicylates, include sulfur, resorcinol, and resorcinol monoacetate. When present, sulfur is typically in an amount of between 0.1 and 10.0% w/w; resorcinol is typically in an amount of between 0.1 and 2.0% w/w, and resorcinol monoacetate is typically in an amount of between 0.1 and 3.0% w/w.

Treatment of Hair Loss/Alopecia/Baldness

When used to treat hair loss, including alopecia and baldness, the compositions commonly include emu oil and one or more of Finasteride and Minoxidil.

Finasteride can be obtained from suppliers such as Cygnus Healthcare Specialties, India. The powder is mixed with Emu Oil in a concentration ranging from about 50 mg to about 100 mg per 100 ml Emu Oil. The combination is applied once or twice daily to area of hair loss on a chronic basis.

Minoxidil Sulphate can be obtained from suppliers such as Loy Pharmalab Incorporated, UK. The powder is mixed with Emu Oil in a concentration ranging from 2% to 5%. The combination is applied once or twice daily to area of hair loss on a chronic basis.

Treatment of Psoriasis, Atopic Dermatitis, and Contact Dermatitis

Steroid creams and lotions can be obtained from many manufacturers. For example, Hydrocortisone 17-butyrate can be obtained from Arrow Chemicals, USA. Hydrocortisone butyrate is mixed with Emu Oil to give a concentration of 0.1%. It is applied locally to the skin lesion twice or three times a day for the treatment of various skin diseases including but not limited to psoriasis, atopic dermatitis, and contact dermatitis.

Treatment of Wrinkles

All Trans Retinol and Retinyl palmitate can be obtained from suppliers such as Paradise Marketing Group, US. The ingredients are mixed with Emu Oil for a final concentration ranging from 1-2%. The combination is applied once or twice daily to wrinkles till satisfactory results are noted.

Acetyl Hexapeptide-3 can be obtained from Lipotec, Spain. The peptide is dissolved in Emu Oil in concentration of 10%. The combination is applied once or twice daily for decreasing wrinkles.

Acetyl Glutamyl Heptapeptide can be obtained from Creative Peptides, US. The peptide is dissolved in Emu Oil in concentration of 10%. The combination is applied once or twice daily for decreasing wrinkles.

Palmitoyl Pentapeptide-3 can be obtained from Creative Peptides, US. The peptide is dissolved in Emu Oil in concentration of 10%. The combination is applied once or twice daily for decreasing wrinkles.

Palmitoyl Oligopeptide can be obtained from Creative Peptides, US. The peptide is dissolved in Emu Oil in concentration of 3-4%. The combination is applied once or twice daily for decreasing wrinkles.

Palmitoyl Terapeptide-3 can be obtained from Creative Peptides, US. The peptide is dissolved in Emu Oil in concentration of 3-4%. The combination is applied once or twice daily for decreasing wrinkles.

Dimethylaminoethanol (DMAE) can be obtained from MD Cosmetics, US. DMAE is dissolved in Emu Oil in concentration of 3%. The combination is applied once or twice daily for decreasing wrinkles.

Idebenone can be obtained from Mahalaxmi Chemi-Pharm, India. DMAE is dissolved in Emu Oil in concentration of 0.5%. The combination is applied once or twice daily for decreasing wrinkles.

Ubiquinone can be obtained from WN Pharmaceuticals, Canada. Ubiquinone is dissolved in Emu Oil in concentration of 1-3%. The combination is applied once or twice daily for decreasing wrinkles.

Treatment of Sun Damage and/or Improvement of Skin Texture

Glycolic Acid can be obtained from suppliers such as Parchem, US. The powder is mixed with Emu Oil for a final concentration ranging from 10% to 80%. The combination is applied once daily to repair sun damage and improve skin texture till satisfactory results are obtained.

Alpha Hydroxy Acids (AHA) can be obtained from suppliers such as Inspire Exports, India. Common AHA include lactic acid, malic acid, citric acid, and tartaric acid. Each powder is mixed with Emu Oil for a final concentration of 12% while keeping pH at 4.5-5.5 using adjusting bases such as sodium hydroxide and hydrochloric acid. More than one AHA is not to be used in combination. The combination is applied once daily to improve skin texture till satisfactory results are obtained. It works by exfoliating the skin and stimulating the cell production in the dermis which results in a "plumper" thicker dermal layer by stimulating collagen and elastin production. This results in a smooth appearance of the skin as well as elimination of fine lines and wrinkles Through the exfoliation process they also work well to remove/decrease hyper-pigmentation which can be hormonally or solar induced.

Beta Hydroxy Acid or Salicylic acid can be obtained from suppliers such as Suntan Industrial Group, Hong Kong. The powder is mixed with Emu Oil for a final concentration of 1-2% while keeping pH at 3-4 using adjusting bases such as sodium hydroxide and hydrochloric acid. The combination is applied once daily to improve skin texture till satisfactory results are obtained. It works by exfoliating the skin and stimulating the cell production in the dermis which results in a "plumper" thicker dermal layer by stimulating collagen and elastin production. This results in a smooth appearance of the skin as well as elimination of fine lines and wrinkles Through the exfoliation process they also work well to remove/decrease hyper-pigmentation which can be hormonally or solar induced.

Kojic acid can be obtained from suppliers such as Parchem, USA. The powder is mixed with Emu Oil for a final concentration of 4%. The combination is applied once daily to improve skin texture till satisfactory results are obtained. It works by exfoliating the skin and stimulating the cell production in the dermis which results in a "plumper" thicker dermal layer by stimulating collagen and elastin production. This results in a smooth appearance of the skin as well as elimination of fine lines and wrinkles Through the exfoliation process they also work well to remove/decrease hyper-pigmentation which can be hormonally or solar induced.

Green Tea can be obtained from suppliers such as Dermaxime, South Africa. The dried extract is mixed with Emu Oil for a final concentration of 10%. The combination is applied once daily to improve skin texture till satisfactory results are obtained as a hydrating agent as well as an anti-oxidant.

UV Protection

When used to treat sun damage, the compositions can further include sunscreen and/or sunblocking agents. The term "sunscreen agent" as used herein defines ultraviolet rayblocking compounds exhibiting absorption within the wavelength region between about 290 and about 400 nm.

The formulation can include, as sunblocking agents, one or more of zinc oxide and titanium dioxide, and, most preferably, a combination of these two agents. The range of these ingredients in the formulations is typically between about 8.10 and about 35.00 weight percent for titanium dioxide, and between about 10 and about 25.65 weight percent for zinc oxide.

Zinc oxide and titanium dioxide are mineral pigments often used for photoprotection, as they are opaque to both UVA and UVB radiation. Although both provide opacity to UV light, titanium dioxide provides 3 to 4 times better coverage and photoprotection. Titanium dioxide is a physical sunscreen providing covering power and UV protection. Zinc oxide is a physical sunscreen that provides covering power and UV protection; reduces sebum production, may promote wound healing, and has powerful antioxidant activity. Zinc oxide also provides additional benefits beyond UV protection. Zinc is a component of at least 70 metalloenzymes and is also needed in protein, DNA, and RNA synthesis. In addition, it is a cofactor for Superoxide Dismutase (SOD), an enzyme providing crucial antioxidant activity and alleviating oxidative stress in cells. Zinc oxide is classified as a Category 1 skin protectant, provides anti-microbial activity, and is thought to be implicated in reducing sebum production and promoting wound healing.

Utilizing a combination of these two compounds will provide ample UV protection, while also supplementing acne treatment and improving skin condition.

Ideally, the particle sizes of these agents are in the micron size or less. Microparticulate (also known as microfine) zinc oxide and titanium dioxide are particulate sunscreen ingredients that absorb broad-spectrum ultraviolet (UV) irradiation.

Treatment of Xerosis and/or Reduction of Scarring

Copper peptide or (Glycine-Histine-Lysine)2-Cu can be obtained from Creative Peptides, US. The peptide is dissolved in Emu Oil in concentration of 10%. The combination is applied once or twice daily for xerosis of the skin, reducing scars, and as an antioxidant.

Skin Rejuvenation and Replacement

Human growth hormone lotion can be used for replacement therapy and for skin rejuvenation at a concentration of 2.5 IU/L. HGH can be obtained from Ferring Pharmaceuticals, US. It is applied topically once in the morning every day chronically as a replacement therapy.

Optional Components

The formulation can also include, in addition to these agents, other cosmetic, dermatological, and pharmaceutical active agents, including, but are not limited to: antioxidants; free radical scavengers; depigmentation agents; reflectants; antimicrobial (e. g., antibacterial) agents; allergy inhibitors; anti-aging agents; anti-wrinkling agents, antiseptics; analgesics; anti-inflammatory agents; fresheners; healing agents; anti infectives; inflammation inhibitors; vasoconstrictors; vasodilators; wound healing promoters; peptides, polypeptides and proteins; skin lightening agents; antifungals; counterirritants; make-up preparations; vitamins; amino acids and their derivatives; herbal extracts; flavoids; sensory markers (i. e., cooling agents, heating agents, etc.); skin conditioners; chelating agents; cell turnover enhancers; nourishing agents; moisture absorbers; sebum absorbers and the like; skin penetration enhancers; and other active ingredients. Other ingredients can include: Water (purified), PEG-4, *Aloe barbadensis* leaf juice, *Allium cepa* (onion) bulb extract, xanthan gum, allantoin, methylparaben, sorbic acid, and fragrance.

Fragrances and Sensory Markers

The formulation described herein also provides synchronizing the release of the sensory markers such as fragrances, flavors, cooling agents, such as menthol derivatives, and heating agents, such as capsaicin. The release of the sensory markers can be used to convey to the consumer the product performance, provide long lasting odor or flavor perception, and signal that a new application of the product is needed.

Conventional fragrance ingredients and perfume ingredients can be used in the release system of the present invention. Selection of any perfume component, or amount of perfume, is based on functional and aesthetic considerations. Examples of usable fragrance and flavor compounds discussed hereinafter, along with their odor characters, and their physical and chemical properties, are given in "Perfume and Flavor Chemicals (Aroma Chemicals)", Steffen Arctander, published by the author, 1969, and in "Common Fragrance and flavor Materials-Preparation, Properties and Uses", Kurt Bauer and Dorotea Garbe, published by VCH Verlagsgesellschaft mbH, 1985, incorporated herein by reference.

Botanical extracts are oak bark extract, walnut extract, tincture of *arnica, hamamelis* extract, ribwort extract, pansy extract, thyme or sage extract; for the treatment of damaged or injured skin, for example, St. John's wort tincture, cone flowers tincture, chamomile flowers extract, or *calendula* flowers tincture; and for the care of exhausted and damaged skin, for example, birch leaves extract, nettle extract, coldsfoot extract, comfrey tincture, horsetail extract, or *aloe vera* extract. Vegetable preparations may also be released from the film layer for the intradermal treatment of diseases, for example, extracts of horse chestnut and butcher's broom in case of vein diseases, or extracts and tinctures of arnica, *calendula*, and capsicum in case of contusions, distortions, or haemorrhages. Vegetable preparations in the system according to the present invention may also be used in transdermal therapy, for example, ginseng extract in case of geriatric complaints; valerian tincture, extracts of melissa and hop to cause a sedative effect in case of superexcitation, sleep disturbances, and stress; extracts of kola and tea to achieve a stimulative effect; or hawthorn extract to stabilize the circulatory system.

Preservatives

Preservatives can desirably be incorporated into the formulations described herein to protect against the growth of potentially harmful microorganisms. While microorganisms tend to grow in the aqueous phase, microorganisms can also reside in the anhydrous or oil phase. As such, preservatives which have solubility in both water and oil are preferably employed in the present compositions. Suitable preservatives for compositions of the present invention are alkyl esters of para-hydroxybenzoic acid. Other preservatives, which can be used include hydantoin derivatives, propionate salts, and a variety of quaternary ammonium compounds.

Appropriate preservatives can be selected to satisfy the preservative challenge test and to provide product stability. Particularly preferred preservatives are methylparaben, imidazolidinyl urea, sodium dehydroacetate, propylparaben, trisodium ethylenediamine tetraacetate (EDTA), and benzyl alcohol. The preservative can be selected based on the consideration of possible incompatibilities between the preservative and other ingredients in the release system.

Preservatives are preferably employed in amounts ranging from about 0.01% to about 2% by weight of the composition.

Vitamins

Various vitamins can be included in the formulations described herein. For example, vitamin A and derivatives thereof, vitamin B2, biotin, pantothenic acid, vitamin K, vitamin D, vitamin E and mixtures thereof can be used.

Antimicrobial and Antifungal Actives

Antimicrobial and antifungal actives can be effective to prevent the proliferation and growth of bacteria and fungi and can be used in the formulations described herein. Non-limiting examples of antimicrobial and antifungal actives include beta-lactam drugs, quinolone drugs, ciprofloxacin, norfloxacin, tetracycline, erythromycin, amikacin, 2,4, 4'trichloro-2'-hydroxy diphenyl ether, 3,4, 4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate, zinc pyrithione; clotrimazole; alantolactone; isoalantolactone; alkanet extract (alaninin); anise; arnica extract (helenalin acetate and 11, 13 dihydrohelenalin); Aspidium extract (phloro, lucinol containing extract); barberry extract (berberine chloride); bay sweet extract; bayberry bark extract (myricitrin); benzalkonium chloride; benzethonium chloride; benzoic acid and its salts; benzoin; benzyl alcohol; blessed thistle; bletilla tuber; bloodroot; bois de rose oil; burdock; butyl paraben; cade oil; CAE (available from Ajinomoto, located in Teaneck, N.J.); cajeput oil; Cangzhu; capsicum frutescens extract; caraway oil; cascarilla bark (sold under the tradename ESSENTIAL OIL); cedarleaf oil; chamomille; chaparral; chlorhexidine gluconate; chlorophenesin; chlorxylenol; cinnamon oil; citronella oil; clove oil; Crinipan AD (available from Climbazole); 2,3-dihydro-farnesol; dehydroacetic acid and its salts; dill seed oil; DOWICIL 200 (available from Dow Chemical, located in Midland, Mich.); echinacea; elenolic acid; epimedium; ethyl paraben; Fo-Ti; galbanum; garden burnet; GERMALL 115 and GERMALL II (available from ISP-Sutton Labs, located in Wayne, N.J.); German chamomile oil; giant knotweed; GLYDANT (available from Lanza, located in Fairlawn, N.J.); GLYDANT PLUS (available from Lanza); grapefruit seed oil; 1,6 hexanediol; hexamidine diisethionate; hinokitiol; honey; honeysuckle flower; hops; immortelle; iodopropynl butyl carbamide (available from Lanza); isobutyl paraben; isopropyl paraben; JM ACTICARE (available from Microbial Systems International, located in Nottingham, NG); juniper berries; KATHON CG (available from Rohm and Haas, located in Philadelphia, Pa.); kojic acid; labdanum; lavender; lemon balm oil; lemon grass; methyl paraben; mint; mume; mustard; myrrh; neem seed oil; ortho phenyl phenol; olive leaf extract (available from Bio Botanica); parsley; patchouly oil; peony root; 1,2 pentandiol; PHENONIP (available from Nipa Labs, located in Wilmington, Del.); phenoxyethanol; phytosphingosine; pine needle oil; PLANSERVATIVE (available from Campo Research); propylparaben; purslane; quillaira; rhubarb; rose geranium oil; rosemary; sage; salicylic acid; sassafras; savory; sichuan lovage; sodium meta bisulfite; sodium sulfite; SOPHOLIANCE (available from Soliance, located in Compiegne, France); sorbic acid and its salts; sphingosine; stevia; storax; sucrose esters; tarmic acid; tea; tea tree oil (cajeput oil); thyme; triclosan; triclocarban; tropolone; turpentine; umbelliferone (antifungal); yucca; and mixtures thereof.

Anti-Inflammatory Agents

Anti-inflammatories can be included in formulations described herein to enhance photoprotection benefits, particularly from UVA.

Suitable steroidal anti-inflammatories include hydrocortisone; non-steroidal anti-inflammatories such as oxicans, salicylates, acetic acid derivatives, fenamates, propionic acid derivatives, pyrazoles, substituted phenyl compounds, 2-naphthyl containing compounds, and natural anti-inflammatories such as *aloe vera*. Examples of anti-inflammatories are described in U.S. Pat. No. 5,487,884, the entire contents of which are incorporated herein by reference.

Anti-Wrinkle, Anti-Skin Atrophy and Skin Repair Actives

Anti-wrinkle, anti-skin atrophy and skin repair actives can be effective in replenishing or rejuvenating the epidermal layer and can be included in formulations described herein. These actives generally provide these desirable skin care benefits by promoting or maintaining the natural process of desquamation.

Nonlimiting examples of anti-wrinkle and anti-skin atrophy actives include vitamin B3 compounds (such as niacinamide and nicotinic acid), salicylic acid and derivatives thereof (such as 5-octanoyl salicylic acid, heptyloxy 4 salicylic acid, and 4-methoxy salicylic acid); sulfur-containing D and L amino acids and their derivatives and salts, particularly the N-acetyl derivatives, a preferred example of which is N-acetyl-L-cysteine; thiols, e. g. ethane thiol; hydroxy acids, phytic acid, lipoic acid; lysophosphatidic acid; skin peel agents (e. g., phenol and the like); Actein 27-Deoxyactein Cimicifugoside (available from Cirnigoside); adapalene; ademethionine; adenosine; aletris extract; alkyl glutathione esters; alkoxyalkoxy alkoxyn benzoic and derivatives; *aloe* derived lectins; amino propane phosphoric acid; 3-aminopropyl dihydrogen phosphate; Amadorine (available from Barnet Products); anise extracts; AOSINE (available from Secma); arginine amino benzoate; ASC III (available from E. Merck, located in Darmstadt, Germany); ascorbic acid; ascorbyl palmitate; asiatic acid; asiaticosides; ARLAMOL GEO™ (available from ICI, located in Wilmington, Del.); azaleic acid; benzoic acid derivatives; bertholletia extracts; betulinic acid; BIOCHANIN A AND BIOPEPTIDE CL (available from Sederma, located in Brooklyn, N.Y.); BIOPEPTIDE EL (available from Sederma); biotin; blackberry bark extract; blackberry lily extracts; black cohosh extract; blue cohesh extract; butanoyl betulinic acid; carboxymethyl1,3 beta glucan; catecholamnines; chalcones; citric acid esters; chaste tree extract; clover extracts; coumestrol; CPC Peptide (available from Barnet Products); daidzein; dang gui extract; darutoside; debromo laurinterol; 1-decanoyl-glycero-phosphonic acid; dehydrocholesterol; dehydrodicreosol; dehydrodieugenol; dehydroepiandersterone; DERMOLECTINE (available from Sederma); dehydroascorbic acid; dehydroepiandersterone sulfate; dianethole; hydroxyl benzoic acid; 2,4 dihydroxybenzoic acid; diglycol guanidine succinate; diosgenin; disodium ascorbyl phosphate; dodecanedioic acid; Ederline (available from Seporga); Enderline (available from Laboratories Seporga); equal; eriodictyol; estrogen and its derivatives; ETF (available from Laboratories Seporga); ethocyn; ELESERYL SH (available from Laboratories Serobiologiques, located in Somerville, N.J.); ENDONUCLEINE (available from Laboratories Serobiologiques); ergosterol; eythrobic acid; fennel extract; fenugreek seed extract; FIBRASTIL (available from Sederma); FIBROSTIMULINES S and P (available from Sederma); FIRMOGEN LS 8445 (available from Laboratories Serobiologiques); formononetin; forsythia fruit extract; gallic acid esters; gamma amino butyric acid; GATULINE RC (available from Gattlefosse, located in Priest, France); genistein; genisteine; genistic acid; gentisyl alcohol; gingko bilboa extracts; ginseng extracts; ginsenoside (RO, R61, R62, R63, Rc, RD, RE, RF, RF-2, RG-I, RG-2); gluco pyranosyl-L-ascorbate; glutathione and its esters; glycitein; hesperitin; hexahydro curcumin; HMGcoenzyme A reductase inhibitors; hops extracts; 11 hydroxy undecanoic acid; 10 hydroxy decanoic acid; 25-hydroxycholesterol; 7-hydroxylated sterols; hydroxyethyl isostearyloxy isopropanolamine; hydroxy-tetra methyl piperidinyloxy; hypotaurine; ibukijakou extract; isoflavone SG 10 (available from Barnet Products); kinetin; kohki extract; L-2-OXOthiazolidine-4-carboxylic acid esters; lactate dehydrogenase inhibitors; 1-lauryl,-lysophosphatidyl choline; lectins; lichochalcone LF15 (available from Maruzen); licorice extracts; lignan; lumisterol; lupenes; luteolin; lysophosphitidic acid; magnesium ascorbyl phosphate; margin; melatonin; melibiose; metalloproteinase inhibitors; methoprene; methoprenic acid; mevalonic acid; MPC COMPLEX (available from CLR); N methyl serine; N methyl taurine; N, Nl-bis (lactyl) cysteamin; naringenin; neotigogenin; odesmethylangoiensin; oat beta glucan; oleanolic acid; pantethine; phenylalanine; photoanethone; piperdine; placental extracts; pratensein; pregnenolone; pregnenolone acetate; pregnenolone succinate; premarin; quillaic acid; raloxifene; REPAIR FACTOR 1 and REPAIR FACTOR FCP (both available from Sederna); retinoates (esters of C2_20 alcohols); retinyl glucuronate; retinyllinoleate; S-carboxymethyl cysteine; SEANAMINE FP (available from Laboratories Serobiologiques); sodium ascorbyl phosphate; soya extracts; spleen extracts; tachysterol; taurine; tazarotene; tempol; thymulen; thymus extracts; thyroid hormones; tigogenin; tocopheryl retinoate; toxifolin; traumatic acid; tricholine citrate; trifoside; uracil derivatives; ursolic acid; vitamin D3 and its analogs; vitamin K; vitex extract; yam extract; yamogenin; zeatin; and mixtures thereof.

Skin Barrier Repair Actives

Skin barrier repair actives are those skin care actives which can help repair and replenish the natural moisture barrier function of the epidermis and can be included in formulations described herein. Non-limiting examples of skin barrier repair actives include Alpha Lipid (available from Lucas Meyer); ascorbic acid; biotin; biotin esters; brassicasterol; caffeine; campesterol; canola derived sterols; Cennamides (available from Ennagram); Ceramax (available from Alban Muller); CERAMAX (available from Quest, located in Ashford, England); CERAMIDE 2 and CERAMIDE H03™ (both available from Sederma); CERAMIDE 11 (available from Quest); CERAMIDE III and IIIB (both available from Cosmoferm, located in Deft, Netherlands); CERAMIDE LS 3773 (available from Laboratories Serobiologiques); CERAMINOL (available from Inocosm); Cerasol and Cephalip (both available from Pentapharm); cholesterol; cholesterol hydroxystearate; cholesterol isostearate; 7 dehydrocholesterol; DERMATEIN BRC and DERMATEIN GSL (both available from Harmel); ELDEW CL 301 AND ELDEW PS 203 (both available from Ajinomoto); Fitobroside (available from Pentapharm); galactocerebrosides; Generol122 (available from Henkel); glyceryl serine amide; hydroxyethyl isostearyl isopropanolamine; lactic acid; Lactomide (available from Pentapharm); lanolin; lanolin alcohols; lanosterol; lauric acid N laurylglucamide; lipoic acid; N-acetyl cysteine; N-acetyl-L-serine; N-methyl-LSerine; Net Sterol-ISO (available from Barnet Products); vitamin B3 compounds (such as niacinamide and nicotinic acid); palmitic acid; panthenol; panthetine; phosphodiesterase inhibitors; PHYTO/CER (available from Intergen); phytoglycolipid millet extract (available from Barnet Products Distributer, located in Englewood, N.J); PHYTOSPHINGOSINE (available from Gist Brocades, located in King of Prussia, Pa.); PSENDOFILAGGRIN (available from Brooks Industries, located in South Plainfield, N.J.); QUESTAMIDE H (available from Quest); serine; sigmasterol; sitosterol; soybean derived sterols; sphingosine; sphingomylinase; S-lactoyl glutathione; stearic acid; Structurine (available from Silah); SUPER STEROL ESTERS (available from Croda); thioctic acid; THSC CERAMIDE OIL (available from Campo Research); trimethyl glycine; tocopheryl nicotinate; vitamin D3; Y2 (available from Ocean Pharmaceutical); and mixtures thereof.

Non-Steroidal Cosmetic Soothing Actives

Cosmetic soothing actives can be effective in preventing or treating inflammation of the skin and can be included in the formulations described herein. The soothing active enhances the skin appearance benefits of the present invention, e. g., such agents contribute to a more uniform and acceptable skin tone or color.

The exact amount of anti-inflammatory agent to be used in the compositions will depend on the particular anti-inflammatory agent utilized since such agents vary widely in potency.

Non-limiting examples of cosmetic soothing agents include the following categories: propionic acid derivatives; acetic acid derivatives; fenamic acid derivatives; biphenylcarboxylic acid derivatives; and oxicams. All of these cosmetic soothing actives are fully described in U.S. Pat. No. 4,985,459 to Sunshine et al., issued Jan. 15, 1991, incorporated by reference herein in its entirety. Non-limiting examples of useful cosmetic soothing actives include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, bucloxic acid, absinthium, acacia, ACTIGEN Y (available from Active Organics), aescin, agrimony, alder buckthorn extract, allantoin, *aloe*, angelica, APT (available from Centerchem), arnica, astragalus, astragalus root extract, AVOCADIN HS-80 (available from Croda), avocado, azulene, Baicalin SR 15 (available from Barnet Products Dist.), Baikal skullcap, baizhu, balm mint, balm of gilead, balsam canada, barley malt, basil, bayberry fruit, bee pollen, bladderwrack, BIODYNES TRF (available from Arch Personal Care), BIOPHYTEX (available from Laboratories Serobiologiques), bisabolol, black cohosh, black cohosh extract blue cohosh, blue cohosh extract, blue flag, boneset, borage, borage oil, bradykinin antagonists, bromelain, burdock root, butterbur, *calendula, calendula* extract, Canadian Willowbark Extract (available from Fytokem), candelilla wax, Cangzhu, canola phytosterols, capsicum, carboxypeptidase, celery seed, celery stem extract, CENTAURIUM (available from Sederma), centaury extract, chamazulene, chamomile, chamomile extract, chaparral, chaste tree, chaste tree extract, chickweed, chicory root, chicory root extract, chirata, chishao, collodial oatmeal, coltsfoot, comfrey, comfrey extract, coneflower, cornflower, CROMOIST CM GLUCAN (available from Croda), CYTOBIOL IRIS A (available from Gattefosse), darutoside, dehurian angelica, devil's claw, divalent metals (such as, magnesium, strontium, and manganese), doggrass, dogwood, dong quai, Eashave (available from Pentapharm), eleuthero, ELHIBIN (available from Pentapharm), ENTELINE 2 (available from Secma), ephedra, epimedium, esculoside; ethacrynic acid, evening primrose, eyebright, Extract LE-100 (available from Sino Lion), Fangfeng, fennel seed extract, feverfew, ficin, fir needle, forsythia fruit, Fytosterol 85 (available from Fytokem), ganoderma, gaoben, gardenia, Gatuline A (available from Gattefosse), gentian, germanium extract, gingko bilboa extract, ginkgo, ginseng extract, GIVOBIO GZn (available from Seppic), goldenseal, gorgonian extract, gotu kola, grape fruit extract, guaiac wood oil, guggal extract, helenalin esters, henna, honeysuckle flower, hops, horehound extract, horsechestnut, horsetail, huzhang, hypericum, Iceland moss, ichthyol, immortelle, ipecac, IRICALMIN (available from Pentapharm), irish moss, ivy, Japanese green tea, job's tears, jojoba, jujube, juniper berry, kava kava, kiwi, kola extract, kumquat, LANACHRYS 28 (available from Lana Tech), lemon oil, LEMON SECRETS (available from Gattefosse), lianqiao, licorice root, ligusticum, ligustrum, lime flower, linden, lovage root, luffa, mace, magnolia flower, mandarin orange, manjistha extract, margaspidin, marshmallow, matricin, meadowsweet, melatonin, MICROAT IRC (available from Nurture), mints, mistletoe, Modulene (available from Seporga), mono or diglucosides of glabridin, mono or diglucosides of gentisin, MTA (5'-deoxy-5'-methythioadenosine), mulberry bark, mullein, mung bean extract, musk, myrrh, N-methyl arginine, nettle, neutral henna, oak bark, oat beta glucan, oat extract, orange, orange blossom, panthenol, papain, papaya, parsley, passion fruit, pear, periwinkle, pine cone, phenoxyacetic acid, peony bark, peony root, Phytoplenolin (available from Bio Botanica), phytosphingosine, plankton, Preregen (available from Pentapharm), prickly ash bark, purslane, QUENCH T (available from Centerchem), quillaia, red clover blossom, red sage, rehmannia, rhubarb, rice bran, roman chamomile, rose, rosemary, rosmarinic acid, royal jelly, rue, rutin, sandlewood, sanqi, sarsaparilla, saw palmetto, SENSILINE (available from Silab), SEPICALM S (available from Seppic), SEPICALM VG (available from Seppic), SIEGESBECKIA (available from Sederma), skullcap, slippery elm, soap bark, spearmint, SPHINGANINE (available from Croda), stearyl glycyrrhetinate, Stimutex (available from Pentapharm), storax, strontium nitrate, sweet birch oil, sweet woodniff, tagetes, tea extract, thyme extract, tienchi ginseng, tocopherol, tocopheryl acetate, triclosan, turmeric, urimei, ursolic acid, VEDACALM (available from Gattefosse), violet, white lily, white pine bark, wild cherry bark, witch hazel, yarrow, yeast extract, yucca, and mixtures thereof.

Anti-Itch Ingredients

Also useful as active ingredients in the present invention are anti-itch ingredients. Non-limiting examples of anti-itch ingredients which are useful in the compositions of the present invention are those selected from the group consisting of *aloe vera*, balm of gilead, beet, pennyroyal, peppermint, soapwort, Stimu-tex (available from Pentapharm); Takanal (available from Ikeda-Distributer); Ichthyol (available from International SourcingDistributor); Oxygenated Glyceryl Triesters (available from Seporgia) and mixtures thereof.

Antioxidants

Representative antioxidants include vitamin E, tocopheryl acetate, betaglucan, coenzyme Q10, butylated hydroxy toluene (BHT), butylated hydroxy anisole (BHA), superoxide dismutase, propylgallate, and the like.

The invention can be further illustrated by the following examples of preferred embodiments thereof, although it will be understood that these examples are included merely for purposes of illustration and are not intended to limit the scope of the invention unless otherwise specifically indicated. All percentages, ratios, and parts herein, in the Specification, Examples, and Claims, are by weight and are approximations unless otherwise stated.

Example 1: Anti-Acne Treatment

A study conducted with Emu Oil and doxycycline was undertaken in volunteers with mild to moderate acne. Sixteen volunteers participated who had mild to moderate acne, and one had severe cystic acne. Within 48 hours of application of the combination, the acne had disappeared. Only the volunteer with severe cystic acne had to apply the combination for five days for the acne to resolve. The efficacy was 100%. This was superior to Emu Oil alone since Emu Oil did not show similar efficacy (rate less than 50%, time to effect a week or longer, and not effective in cystic acne). There are no tropical formulations of doxycycline to compare with. On histological examination, doxycycline was found in the dermis within 15 minutes of topical application.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed:

1. A composition for use in treating hair loss, consisting of emu oil and one or more additional active ingredients selected from the group consisting of Finasteride and Minoxidil, wherein when the active ingredient is Finasteride, the Finasteride is present at a concentration of between about 50 and about 100 mg/100 ml emu oil, and when the active agent is Minoxidil, the Minoxidil is present at a concentration of 2-5% by weight of the composition.

2. The composition of claim 1, wherein the active ingredient is Finasteride, and the Finasteride is present at a concentration of between about 50 and about 100 mg/100 ml emu oil.

3. The composition of claim 1, wherein the active ingredient is Minoxidil, wherein the Minoxidil is present at a concentration of 2-5%.

4. A method for treating hair loss, comprising topically administering a composition of claim 1 to the scalp of a patient in need of treatment thereof.

5. A method for treating hair loss, comprising topically administering a composition of claim 2 to the scalp of a patient in need of treatment thereof.

6. A method for treating hair loss, comprising topically administering a composition of claim 3 to the scalp of a patient in need of treatment thereof.

* * * * *